United States Patent [19]
Fredriksen

[11] Patent Number: 6,139,502
[45] Date of Patent: Oct. 31, 2000

[54] ULTRASONIC TRANSDUCER PROBE AND HANDLE HOUSING AND STAND-OFF PAD

[75] Inventor: Paul Sverre Fredriksen, Tolvsroed, Norway

[73] Assignee: G.E. Vingmed Ultrasound A/S, Horten, Norway

[21] Appl. No.: 09/223,403

[22] Filed: Dec. 30, 1998

[51] Int. Cl.[7] .................................................. A61B 8/00
[52] U.S. Cl. ........................................................ 600/459
[58] Field of Search .................................. 600/437, 459, 600/443; 73/632–633

[56] References Cited

U.S. PATENT DOCUMENTS

| | | |
|---|---|---|
| D. 369,307 | 4/1996 | Imling et al. . |
| 4,641,657 | 2/1987 | Ellis ........................................ 600/459 |
| 4,674,517 | 6/1987 | Barnes et al. ........................... 600/459 |
| 4,796,632 | 1/1989 | Boyd et al. .............................. 600/459 |
| 4,815,470 | 3/1989 | Curtis et al. ............................ 600/459 |
| 4,898,177 | 2/1990 | Takano et al. .......................... 600/459 |
| 5,165,415 | 11/1992 | Wallace et al. ........................ 600/459 |
| 5,170,790 | 12/1992 | Lacoste et al. ........................ 600/459 |
| 5,299,578 | 4/1994 | Rotteveel et al. . |
| 5,335,663 | 8/1994 | Oakley et al. .......................... 600/459 |
| 5,351,691 | 10/1994 | Brommersma . |
| 5,381,795 | 1/1995 | Nordgren et al. . |
| 5,482,047 | 1/1996 | Nordgren et al. . |
| 5,671,747 | 9/1997 | Connor ................................... 600/459 |
| 5,792,059 | 8/1998 | Furia et al. ............................. 600/459 |

*Primary Examiner*—Francis J. Jaworski
*Attorney, Agent, or Firm*—McAndrews Held and Malloy; Christian G. Cabou; Phyllis Y. Price

[57] ABSTRACT

An ultrasonic transducer probe and handle housing including an elongated base having a longitudinal axis and a multiple-angled handle. A first stem portion extends from the base along a first stem axis that forms an inclined angle with the base longitudinal axis. A second stem portion merges with the first stem portion and extends along a second stem axis that forms an inclined angle with the first stem axis. In an alternative embodiment, the probe and handle housing includes a handle having proximal and distal ends. In this embodiment, the proximal end is coupled to the base and the distal end extends away from the base in a lateral direction with respect to the longitudinal axis of the base. Additionally, a stand-off pad may be removably affixed to the base and may be adapted to contain a fluid.

43 Claims, 5 Drawing Sheets

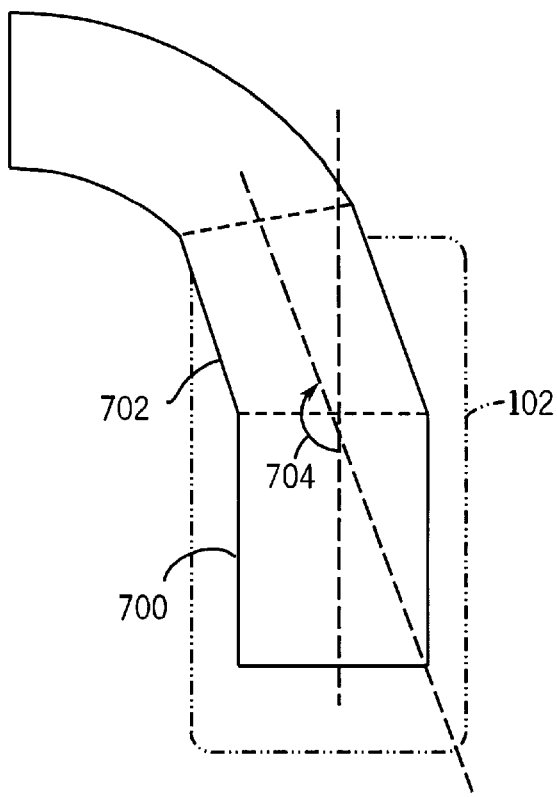
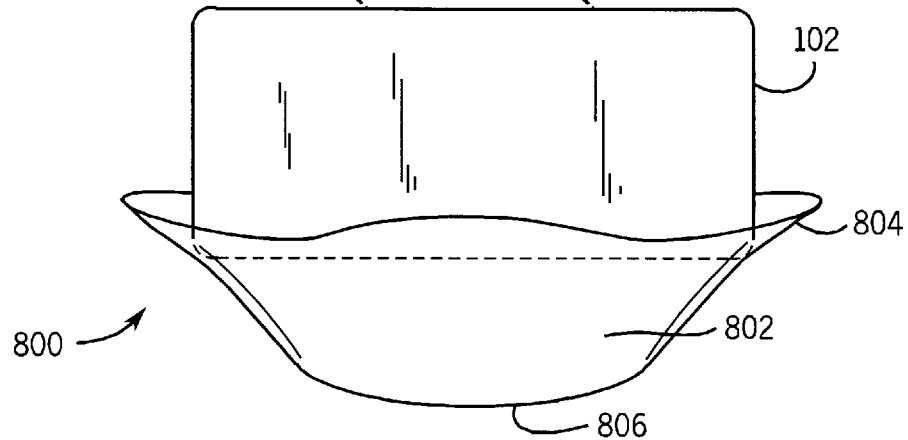

ULTRASONIC TRANSDUCER PROBE AND HANDLE HOUSING AND STAND-OFF PAD

CROSS-REFERENCE TO RELATED APPLICATIONS

Not applicable.

STATEMENT REGARDING FEDERALLY SPONSORED RESEARCH OR DEVELOPMENT

Not Applicable.

BACKGROUND OF THE INVENTION

The present invention generally relates to ultrasound probes and in particular to ultrasound probe and handle housings and stand-off pads for sue with such housings.

Ultrasonic diagnostic imaging probes generally have been used in the past to image anatomical structures within the body. Ultrasonic probes have been used in the past during non-invasive procedures (such as trans-thoracic probes), during invasive procedures (such as trans-esophageal echocardiography (TEE) probes and trans-vaginal probes), and during surgical procedures (i.e., intraoperative probes).

When using ultrasonic probes, it is important that the hand of the physician using the probe not obscure the site being examined. While the probe is imaging, for example, a physician must be able to accurately determine and maintain the position of the probe while looking at a monitor displaying the information obtained from the probe.

Past intraoperative ultrasound probes have provided, for example in U.S. Pat. No. 5,381,795 to Nordgren et al., an intraoperative ultrasound probe having a transducer section and an angled handle section that form an obtuse angle with respect to one another. The shape of the handle was used in an attempt to permit the physician to grasp the probe without blocking the physician's view of the surgical site. Surgical procedures in which intraoperative probes have been used include vascular surgery and transplant surgery. Dining vascular surgery, ultrasonic imaging probes can be used to image and diagnose the interior of carotid arteries. In transplant surgery, intraoperative ultrasonic probes can be used to verify successful attachment and function of renal arteries. Intraoperative ultrasound probes are preferably small and as easy to manipulate as surgical instruments.

Past trans-vaginal probes have provided, for example in U.S. Pat. No. 4,742,829 to Law et al., a handle offset from the central axis of the probe. The shape of the handle was used in an attempt to free the space around the entrance of a needle guide to thereby permit manipulation of the needle by hand. The probes disclosed in the above-referenced patents did not, however, present a probe having a multiple-angled handle section.

Past TEE probes have provided, for example in U.S. Pat. No. 5,351,691 to Brommersma, a flexible tube having at one end a probe head. The flexible end part is connected to a housing to allow a probe head to be bent forwards or backwards.

A need remains for an improved ultrasonic probe housing that enables a physician to accurately determine and maintain the position of the probe during use. A need also remains for an improved ultrasonic probe housing that allows the physician to move the probe while maintaining its orientation without having to view the probe to ensure it is oriented properly. It is an object of the present invention to meet these needs.

Additionally, in the past, users of ultrasonic technology have noticed that ultrasound probes do not image well when they are used in close proximity to the surface of the tissue being monitored. As a result, past ultrasound probes have placed a material of similar sound velocity as anatomical tissue between the probe and the patient as a standoff (i.e., a standoff between the probe and patient), with the material generally being 1 to 4 cm in thickness. Moreover, the quality of ultrasound images is adversely affected by the presence of a moving organ, due to, for example, blood pulsation. Ultrasound images are also adversely affected by the lack of an effective acoustic coupling due to a fixed (usually flat) transducer or probe surface and a curved or irregular shape of an anatomic structure, such as a heart, artery or other organ.

One way in which such standoffs have been formed is by using a metal or plastic structure to hold a thin plastic or elastomer bag filled with a coupling material. Additionally, rigid plastics have been used as containers for the coupling fluid with acoustic windows made of thin plastic films on the container for the transmission of ultrasound through the container. An adapter and standoff for an ultrasound probe including a first compression molded coupler portion and a second compression molded receptacle portion is disclosed in, for example, U.S. Pat. No. 4,796,632 to Boyd et al. The first and second portions were assembled to define a fluid cavity for coupling ultrasound waves and a receptacle for receiving a probe head.

Past ultrasound technology has not, however, presented an ultrasonic probe having a stand-off balloon affixable to the probe that can avoid the aforementioned problems. A need remains for such a probe.

BRIEF SUMMARY OF THE INVENTION

In an exemplary embodiment of the invention, an ultrasonic transducer probe and handle housing includes an elongated base having a longitudinal axis. A first stem portion extends from the base along a first stem axis that forms an inclined angle, i.e., an angle between 0° and 90°, with respect to the longitudinal axis of the base. A second stem portion merges with the first stem portion. The second stem portion extends along a second stem axis that forms an inclined angle with the first stem axis.

BRIEF DESCRIPTION OF THE SEVERAL DRAWINGS

FIG. 7 is a top plan of the probe handle with the probe base shown schematically.

FIG. 8 is a side view of the stand-off pad and probe and handle housing base with the probe stem shown schematically.

DETAILED DESCRIPTION OF THE INVENTION

Figure 1:
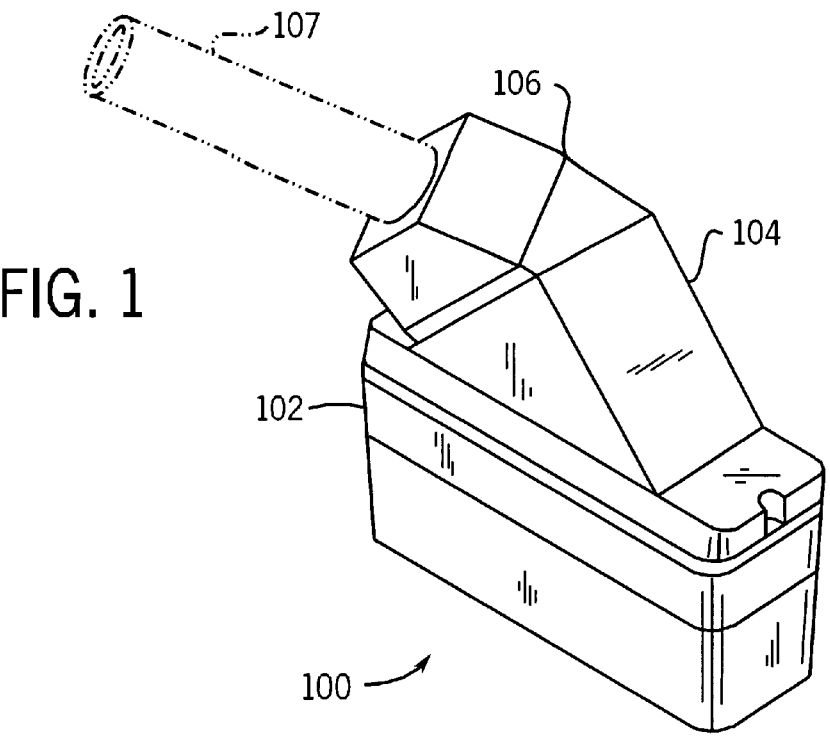
FIG. 1 is a perspective view of a probe and handle housing according to a particular embodiment of the present invention.

Turning now to FIG. 1, there is shown an ultrasonic probe and handle housing 100. The housing includes a base 102 and a stem extending from the base for handling the probe. The stem includes a first stem portion 104 and a second stem portion 106. A probe cable 107 extends from the second stem portion 106.

Figure 1A:
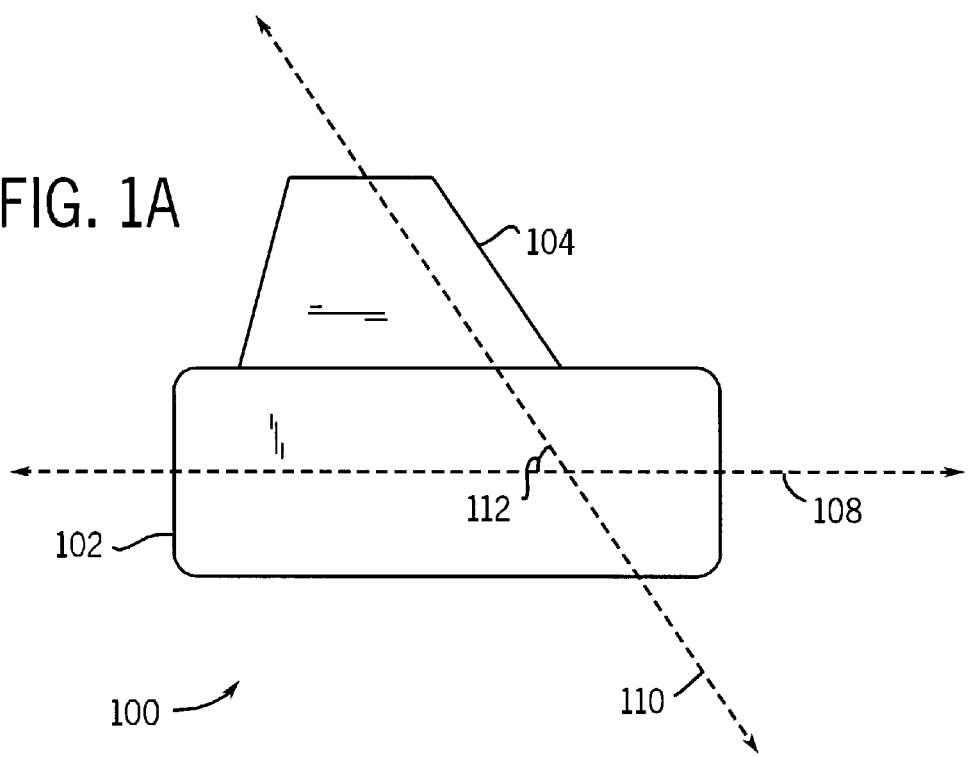
FIG. 1A is a side view of the probe and handle housing showing the base and first stem portion diagrammatically.

Turning to FIG. 1A, a view of the base 102 and first stem portion 104 of the housing 100 are shown. The longitudinal axis of the base 108, the longitudinal axis of the first stem portion 110, and the inclined angle 112 at which the two axes intersect are also shown.

Figure 1B:
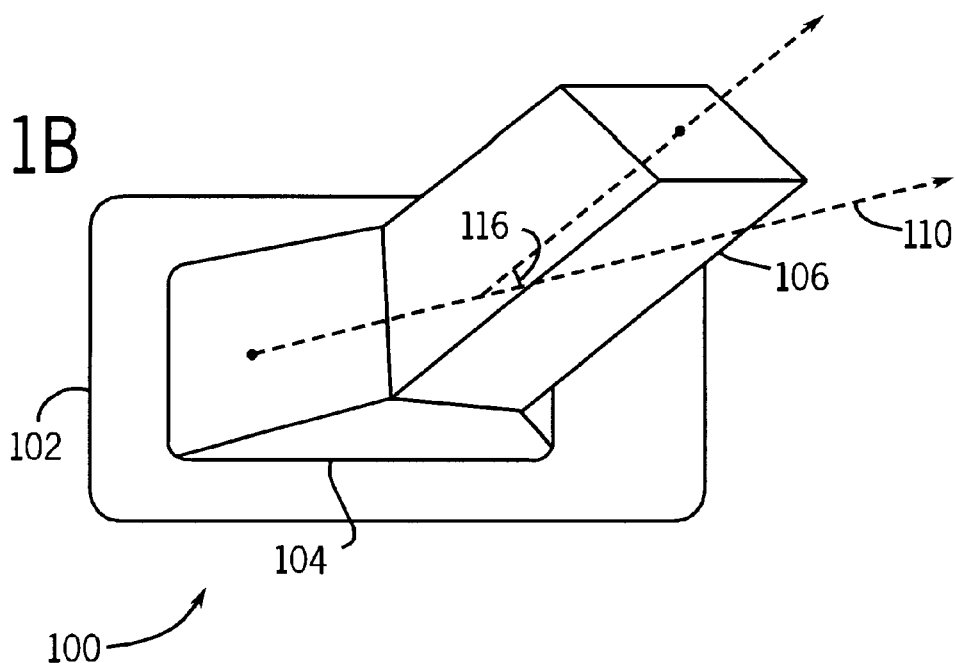
FIG. 1B is a top plan of the probe and handle housing.

Turning to FIG. 1B, a top view of the probe and handle housing 100 is presented. The longitudinal axis along which the first stem portion extends 110, the longitudinal axis along which the second stem portion extends 114, and the angle 116 at which the axes intersect are shown.

Turning back to FIG. 1, a base 102 is provided for use with ultrasonic imaging technology. In the present embodiment, the lower surface of the probe is rectangular in shape, although this is not required. The first stem portion 104 extends from the base 102. The first stem portion 104 may extend from the base 102 in one of several methods such as, for example, the stem portion 104 may be affixed to the base 102 or the stem portion 104 and base 102 may be integrally molded. The first stem portion 104 may extend from the base 102 at any portion of the base 102, including at the center of the upper face of the base 102.

Referring still to FIG. 1, a second stem portion 106 is merged with the first stem portion 104, preferably to the section of the first stem portion opposite the section of the first stem portion that extends from the base 102. The second stem portion 106 may be merged with the first stem portion 104 using one of several methods such as, for example, the second stem portion 106 may be affixed to the first stem portion 104 or the first and second stem portions 104, 106 may be integrally molded.

Preferably, the first and second stem portions 104, 106 are rigid. To meet this preferred construction, the stem portions 104, 106 may be made of, for example, a hard plastic. If the probe housing is suited for use, for example, as an intraoperative probe housing, the housing 100 should be suitable for use in a sterile environment, such as in an operating room during surgery.

Figure 6:
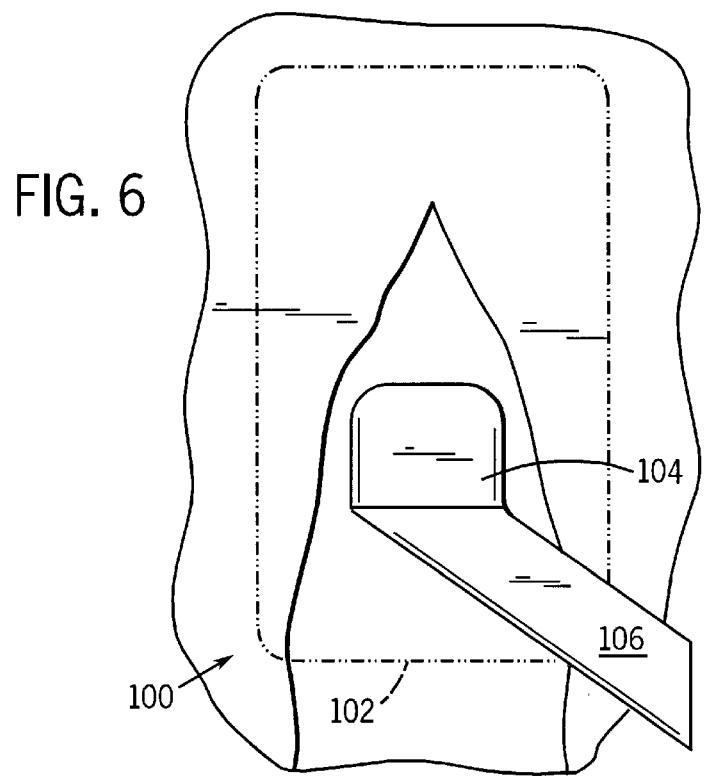
FIG. 6 is a top view of the probe and handle housing being implemented intraoperatively according to a particular embodiment of the present invention.

As shown in FIG. 1A, the first stem portion 104 in this embodiment extends from the base 102 so that the first stem portion 104 extends along a longitudinal axis 110. The longitudinal axis 110 of the first stem portion 104 preferably forms an inclined angle 112 with respect to the longitudinal axis 108 of the base, as shown in FIG. 1A. This relationship between the longitudinal axes of the base 108 and first stem portion 110 permits, for example, the front portion of the base 102 to extend under a portion of unincised skin during an operation, as shown in FIG. 6. A physician may therefore obtain ultrasonic image information about anatomical structures above which the skin has not been cut. This relationship also permits the physician using the probe to be able to more accurately determine the position of the probe relative to the anatomical structure being monitored since the stem portions 104, 106 form a handle for the physician to hold onto the probe during usage. As a result, the physician is able to maintain an accurate sense of direction of the ultrasound beam and its relative position to the anatomical structure the physician is imaging. Additionally, if, for example, the probe handle were to extend from the base at a perpendicular angle (i.e., vertically with respect to the base), the physician's fingers would be more likely to get in the way of the physician's line of sight to the portion of the body begin monitored.

As shown in FIG. 1B, the second stem portion 106 is, in the illustrated embodiment, merged with the first stem portion 104 so that the second stem portion 106 extends along a longitudinal axis 114. The longitudinal axis 114 of the second stem portion preferably forms an inclined angle 116 with respect to the longitudinal axis 110 of the first stem portion, as shown in FIG. 1B. This relationship between the first and second stem portions 104, 106 permits the physician using the probe to more accurately determine the position of the probe relative to the anatomical structure being monitored than if only a first stem portion were present. Specifically, the inclined angle 116 permits the physician to accurately maintain the orientation of the probe while viewing, for example, a monitor displaying an output from the probe. The angulation of the second stem portion 106 also allows the physician to hold the probe, at least in part, by the second stem portion 106 without placing his or her fingers in the line of sight to the base of the probe.

Figure 1C:
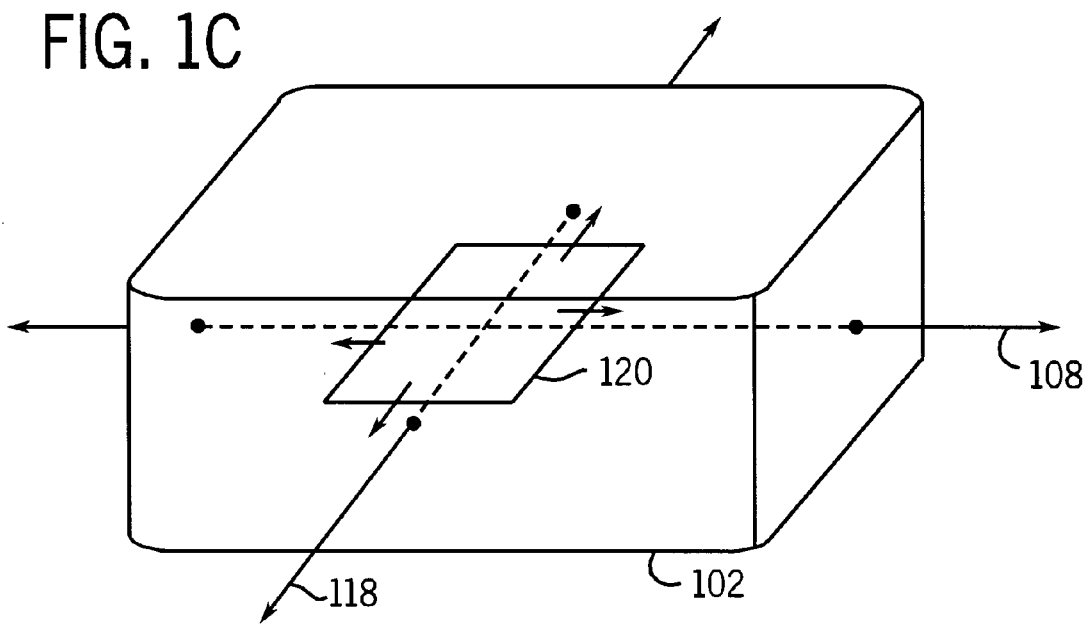
FIG. 1C is a perspective view of the probe and handle housing base.
Figure 2:
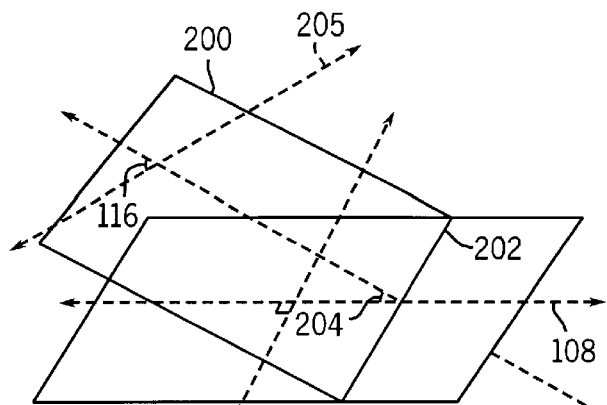
FIG. 2 is a perspective view of the planes in which the axes of the probe and handle housing base, first stem portion, and second stem portion reside.
Figure 3:
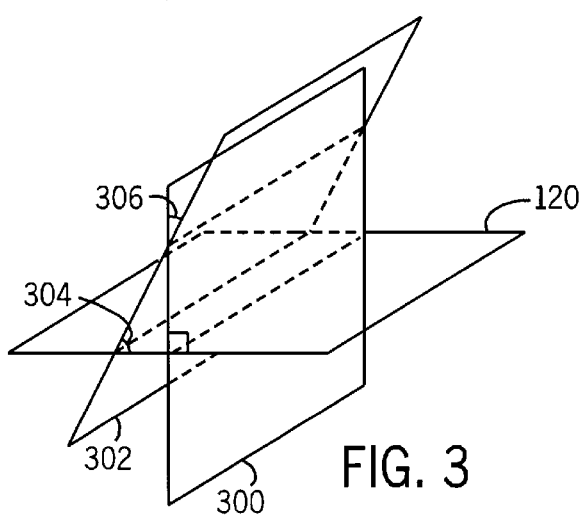
FIG. 3 is a perspective view of the planes in which the axes of the first and second stem portions reside.

Turning now to FIGS. 1C, 2 and 3, FIG. 1C presents the base 102 of the housing 100, including the longitudinal axis of the base 108, the lateral axis of the base 118, and the plane 120 in which the longitudinal and lateral axes may reside. FIG. 2 illustrates the inclined plane 200 in which the first and second stem portions 104, 106 may reside. Also presented are the line of intersection 202 of these two planes, the angle of intersection 204 of these two planes, and the longitudinal axis of the second stem portion 205 (which, in FIG. 2, resides in the inclined plane 200). FIG. 3 presents the planes in which the axes of the base 120, first stem portion 300, and second stem portion 302 may reside.

As shown in FIG. 1C, the base 102 may be constructed such that the lateral 118 and longitudinal 108 axes of the base reside in a first plane 120. Preferably, the first stem axis 104 extends from the basin a second plane 300, shown in FIG. 3, that is substantially perpendicular to the first plane 120, in which the axes of the base 108, 118 reside. This perpendicular relationship between the planes 120, 300 permits the probe to be used in a manner that will cause minimal agitation, including tearing, to an incised portion of the tissue during, for example, intraoperative use, as can be seen from FIG. 6.

In the preferred construction, the second stem portion 106 resides in a third plane 302 that forms an inclined angle 304 with the first plane and an inclined angle 306 with the second plane, as shown in FIG. 3. That is, the second stem portion 106 preferably extends, at least in part, laterally away from the second plane 300 while it extends, at least in part, vertically away from the base 102 of the probe.

In the embodiment illustrated in FIG. 2, the first and second stem portions 104, 106 lie in an inclined plane 200 with respect to the plane 120 in which the longitudinal and lateral axis of the base reside. The inclined plane 200 intersects the first plane 120 along a line 202 parallel to the lateral axis of the base. That is, the first and second stem portions 104, 106 in this embodiment gradually move away from the base at a constant, inclined angle 202, even after the transition from the first stem portion 104 to the second stem portion 106 (shown by angle 116).

Figure 4:
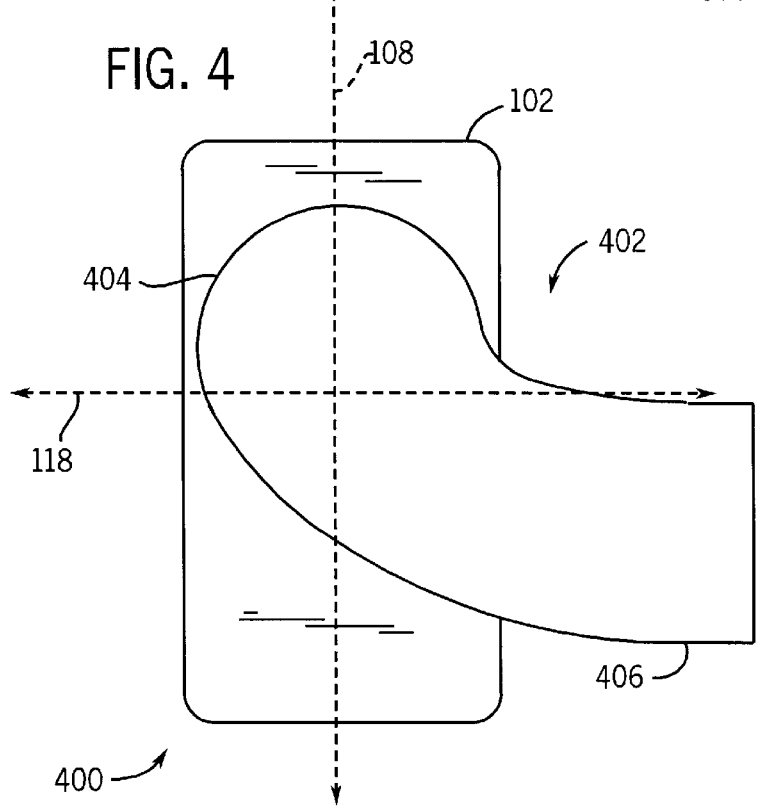
FIG. 4 is a top plan of the probe and handle housing according to an alternative embodiment of the present invention.
Figure 5:
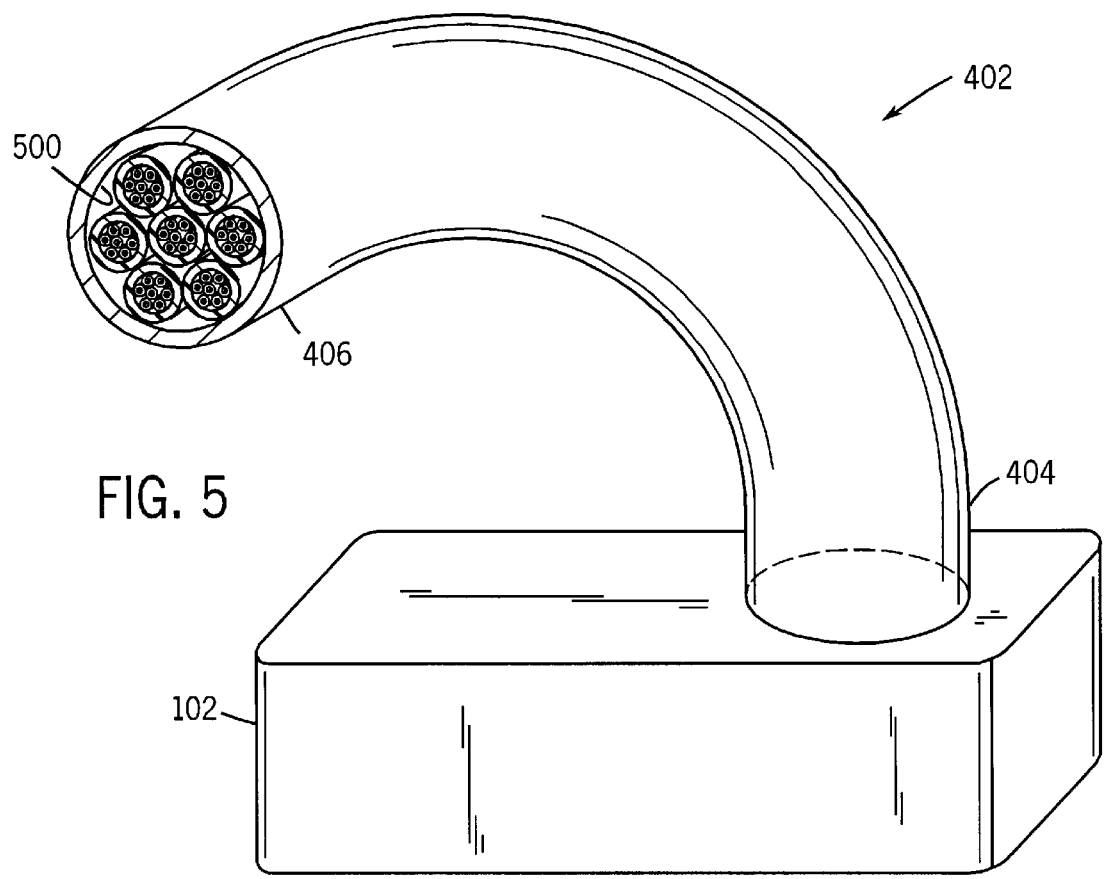
FIG. 5 is a perspective view of the probe and handle housing.

Turning now to FIGS. 4 and 5, those Figures present a probe and handle housing 400 including a base 102 and a handle 402 according to another embodiment of the invention. The illustrated base 102 is elongated and has longitudinal 108 and lateral 118 axes. The handle 402 of the housing 400 has a proximal end 404 and a distal end 406. The proximal end 404 of the handle is coupled to the base 102. The distal end 406 of the handle, however, extends away from the base 102 in a lateral direction with respect to the longitudinal axis 108 of the base. In the illustrated embodiment, the handle 402 is curvilinear in shape and, in fact, forms a continuous curvilinear profile.

As with a previously-referenced embodiment, this shape permits the physician to be able to more accurately determine where the probe is positioned relative to the anatomical structure being imaged. Specifically, if the physician grips the handle 402 near the distal end 406, the physician may have an unobstructed view of the proximal end 404 of the handle and, more importantly, of the base 102 of the probe. Additionally, in the illustrated embodiment of FIG. 5, the handle 402 has a substantially hollow interior 500. The substantially hollow interior 500 permits, for example, the multifilament cable shown in FIG. 5 to lead to a connector suitable for connecting the probe to an ultrasonic diagnostic system which drives the transducer of the probe and receives ultrasonic echo signals from the transducer. The probe cable 107 shown in FIG. 1 may be provided, for example, to contain the multifilament cable.

Preferably, the distal end 406 of the handle extends away from the base 102 at an inclined angle with respect to the base 102. When the probe is used intraoperatively, this shape permits the physician to more easily grip the handle 402 of the probe without agitating or interfering with the incised area of the patient. The probe may also be formed such that the proximal end 404 of the handle extends away from the base 102 at an inclined angle with respect to the base. Preferably, both the proximal 404 and distal 406 ends extend away from the base at an inclined angle. This preferred structure permits as short of a handle 402 as possible while still allowing the physician to properly grip the handle 402 without obstructing the physician's view of the probe.

In the illustrated embodiment of FIG. 4, the longitudinal and lateral axes 108, 118 of the base reside in a first plane 120. The proximal end 404 initially extends from the base 102 in a second plane 300 that is approximately perpendicular to the first plane, as shown in FIG. 3. When used intraoperatively, this illustrated structure permits the handle to extend from the probe in a manner causing minimal agitation of the incised area of the patient, similarly to the embodiment shown in FIG. 6. In the illustrated embodiment, the distal end 406 of the handle lies in an inclined plane that intersects the first plane along a line of intersection that is parallel to the lateral axis of the base; for example, the inclined plane 200 shown in FIG. 2.

In the present embodiment, the handle 402 may be formed by multiple handle portions, such as the first 700 and second 702 handle portions of FIG. 7, that intersect at an obtuse angle 704. As a result, it can be seen that a handle 402 according to the present invention may be partially curved in shape and partially straight.

According to yet another embodiment of the invention, whichever of the aforementioned embodiments is used, a stand-off pad 800 may be removably affixed to the base 102, as shown in FIG. 8. The stand-off pad 800 may be adapted to contain a fluid 802. Preferably, the fluid 802 contained within the stand-off pad 800 is composed of a material having a similar sound velocity to anatomical tissue. This does permit the ultrasound probe to get a better image of the anatomical structure sought to be imaged, recognizing the fact that ultrasonic probes typically do not image well in close proximity to the surface of the tissue being monitored. However, there are two other purposes for the stand-off pad 800 of the present invention. First, the stand-off pad provides acts as a "pillow" because it provides a damping effect between a pulsing anatomical structure and the probe. The pulsing may be caused by, for example, blood pulsation. Second, the stand-off pad 800 improves the acoustic, coupling between a fixed (usually flat) surface of a probe and an often curved and/or irregularly shaped anatomical structure, such as a heart, artery, or other organ. The stand-off pad 800, with the fluid 802 contained therein, is preferably pliable so that the damping and coupling can be effected.

The stand-off pad 800 shown in FIG. 8 is balloon-shaped, having a neck-like portion 804 and a bag-like portion 806. Although this shape is not required, when the stand-off pad 800 is so shaped, the neck-like portion 804 may be removably affixed to the base. In the illustrated embodiment, the inner perimeter of the neck-like portion 804 receives the lower surface of the base 102. Preferably, a substantially fluid-impermeable seal is formed where the neck-like portion 804 is removably affixed to the base 102. Additionally, in the illustrated embodiment, it is the bag-like portion 806 of the stand off pad 800 that is adapted to contain a fluid 802.

Whichever of the embodiments is used, however, the handle may also be constructed so that it does not have a substantially hollow interior. The probe cable 107 may exit the handle closer to the base 102 than illustrated in FIG. 1. Alternatively, the probe cable 107 may exit the base 102 separately from the handle (not pictured). The handle may also be removably affixed to the base 102, so that the handle can be detached from the base 102. Moreover, the handle may be formed such that it is flexible and bendable to a user desired shape.

While particular embodiments of the invention have been shown, it will be understood, of course, that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and the scope of the invention.

What is claimed is:

1. An ultrasonic transducer probe and handle housing for intraoperative use comprising:
    an elongated base having a longitudinal axis;
    a first stem portion extending from said base, said first stem portion extending along a first stem axis that forms an inclined angle with respect to the longitudinal axis of said base; and
    a second stem portion merging with said first stem portion, said second stem portion extending along a second stem axis that forms an inclined angle with said first stem axis;
    wherein said elongated base has a center along its longitudinal axis and said first stem portion extends from said base at approximately the center of said base.

2. The housing of claim 1 wherein said base comprises a surface for transmitting ultrasound waves.

3. The housing of claim 1 wherein said first and second stem portions are approximately equal in length.

4. The housing of claim 1 wherein said first and second stem portions are rigid.

5. The housing of claim 1, further comprising a flexible cushioned pad secured to a periphery of said base damping external forces caused by an anatomic structure.

6. The housing of claim 5 wherein said flexible cushioned pad is balloon-shaped, having a neck-like portion and a bag-like portion.

7. The housing of claim 5 wherein said stand-off pad is balloon-shaped, having a neck-like portion and a bag-like portion.

8. The housing of claim 7 wherein said neck-like portion is removably affixed to said base, thereby forming a substantially fluid-impermeable seal where said neck-like portion is removably affixed to said base.

9. The housing of claim 7 wherein said bag-like portion of said flexible cushioned pad is adapted to contain a fluid.

10. The housing of claim 5, wherein said cushioned pad is secured directly to a periphery of said base.

11. The housing of claim 5, wherein said flexible cushioned pad absorbs relative motion caused by motion of the heart.

12. The housing of claim 1 wherein said base is adapted for intraoperative use.

13. The housing of claim 1 wherein said first stem portion removably extends from said base.

14. The housing of claim 1 wherein said second stem portion removably merges with said first stem portion.

15. The housing of claim 1 wherein said first and second stem portions are flexible so that said stem portions are adaptable to be molded to a user-desired shape.

16. A unitary ultrasonic transducer probe and handle housing comprising:
   an elongated base having longitudinal and lateral axes in a first plane;
   a first stem portion, extending from said base and integral with said base, having a longitudinal axis that forms an inclined angle with the first plane, said first stem portion extending from said base in a second plane that is approximately perpendicular to the first plane; and
   a second stem portion, merging with said first stem portion, having a longitudinal axis that forms an inclined angle with respect to the second plane.

17. The housing of claim 16 wherein the second plane intersects said first plane along said longitudinal axis of said base.

18. The housing of claim 16 wherein said second stem portion extends from said first stem portion in a third plane that forms an inclined angle with the first plane and an inclined angle with the second plane.

19. The housing of claim 18 wherein said inclined angle between the third plane and the second plane is approximately 45°.

20. The housing of claim 18 wherein said inclined angle between the third plane and the second plane is approximately the same angle as the angle the longitudinal axis of said first stem portion forms with respect to the first plane.

21. The housing of claim 16 wherein said base has a center along its longitudinal axis and said first stem portion extends from said base at approximately the center of said base.

22. The housing of claim 16 wherein said first and second stem portions are approximately equal in length.

23. The housing of claim 16 wherein the inclined angle between the longitudinal axis of said first stem portion and the first plane is approximately 45°.

24. The housing of claim 16 wherein said first and second stem portions lie in an inclined plane that intersects the first plane along a line parallel to said lateral axis.

25. The housing of claim 16 wherein said first and second stem portions are rigid.

26. The housing of claim 16 further comprising a flexible cushioned pad removably secured to said elongated base, said flexible pad damping external forces caused by an anatomic structure.

27. The housing of claim 26 wherein said cushioned pad is secured directly to said elongated base.

28. The housing of claim 26, wherein said cushioned pad absorbs relative motion caused by motion of the heart.

29. An ultrasonic transducer probe and handle housing for use with a cable connector to an ultrasonic imaging system comprising:
   an elongated base having longitudinal and lateral axes; and
   a curvilinear handle affixed to said base having proximal and distal ends, wherein
      said proximal end is coupled to said base, and
      said distal end extends away from said base in a lateral direction with respect to the longitudinal axis of said base; and
   wherein said distal end extends away from said base so as to form a continuous curvilinear profile.

30. The housing of claim 29 wherein said distal end extends away from said base at an inclined angle with respect to said base.

31. The housing of claim 29 wherein:
   the longitudinal and lateral axes of said base reside in a first plane;
   said proximal end initially extends from said base in a second plane that is approximately perpendicular to said first plane.

32. The housing of claim 31 wherein the first and second planes intersect along the longitudinal axis of said base.

33. The housing of claim 29 wherein said distal end of said handle extends from said base so as to form a curvilinear shaped handle.

34. The housing of claim 33 wherein said distal end of said handle extends from said base so as to give said handle a substantially continuous profile.

35. The housing of claim 29 wherein:
   the longitudinal and lateral axes of said base reside in a first plane; and
   said distal end lies in an inclined plane that intersects the first plane along a line of intersection that is parallel to the lateral axis of said base.

36. The housing of claim 29 wherein said handle is defined by at least first and second handle portions intersecting in an obtuse angle.

37. The housing of claim 29 wherein said handle is rigid.

38. The housing of claim 29 wherein the base is adapted for intraoperative use.

39. The housing of claim 29, further comprising a pliable intermediary damping member secured to said base, said damping member absorbing relative motion between said base member and an anatomical structure containing said damping member, said damping member having an interior cavity for receiving an acoustic coupling fluid.

40. The housing of claim 39 wherein said intermediary damping member is balloon-shaped, having a neck-like portion and a bag-like portion.

41. The housing of claim 40 wherein said neck-like portion is removably affixed to said base, thereby forming a substantially fluid-impermeable seal where said neck-like portion is removably affixed to said base.

42. The housing of claim 29 wherein said handle is removably affixed to said base.

43. The housing of claim 29 wherein said handle is flexible so that said handle is adaptable to be molded to a user-desired shape.

* * * * *